(12) United States Patent
Bleyle

(10) Patent No.: US 6,486,944 B1
(45) Date of Patent: Nov. 26, 2002

(54) FLUID-SEALED REFRACTOMETER HAVING DATA TRANSMISSION MEANS

(75) Inventor: Kyle R. Bleyle, Lancaster, NY (US)

(73) Assignee: Leica Microsystems Inc., Depew, NY (US)

( * ) Notice: Subject to any disclaimer, the term of this patent is extended or adjusted under 35 U.S.C. 154(b) by 0 days.

(21) Appl. No.: 09/877,591

(22) Filed: Jun. 8, 2001

(51) Int. Cl.$^7$ ................................................ G01N 21/41
(52) U.S. Cl. ........................ 356/128; 356/135; 356/134
(58) Field of Search ................................ 356/128, 129, 356/130, 131, 132, 133, 134, 135, 136, 137; 250/577, 573–576

(56) References Cited

U.S. PATENT DOCUMENTS

| | | | | |
|---|---|---|---|---|
| 4,243,321 A | * | 1/1981 | Okuda et al. | 356/135 |
| 4,381,895 A | * | 5/1983 | Hughes et al. | 356/134 |
| 4,640,616 A | * | 2/1987 | Michalik | 356/136 |
| 4,890,916 A | * | 1/1990 | Rainer | 356/135 |
| 5,969,808 A | * | 10/1999 | Cotton et al. | 356/135 |
| 6,067,151 A | * | 5/2000 | Salo | 356/136 |
| 6,172,746 B1 | * | 1/2001 | Byrne et al. | 356/135 |
| 6,256,129 B1 | * | 7/2001 | Kim et al. | 359/159 |

FOREIGN PATENT DOCUMENTS

JP 08 280 625 * 10/1996

OTHER PUBLICATIONS

MISCO Digital Fiberoptic Refractometer—We're Changing the Way you Look at Refractometers!, http://www.misco.com/Digital/digital.html, May 16, 2001, pp. 1 and 2.
Index Instruments For Refractometers And colorimeters, Index Instruments, Refractometers—Colorimeters—Sampling Systems, GPR 12–70 General Purpose Refractometer, http://www.indexinstruments.com/gpr.htm, May 16, 2001, pp. 1 and 2.

* cited by examiner

Primary Examiner—Frank G. Font
Assistant Examiner—Sang H. Nguyen
(74) Attorney, Agent, or Firm—Simpson & Simpson, PLLC

(57) ABSTRACT

A hand-held automatic refractometer comprises a completely fluid-sealed housing enclosing a wireless transmitter for transmitting digital measurement data to a remote computer having a corresponding receiver connected thereto. The refractometer housing protects the internal components, including the transmitter, from damage caused by test fluids and cleaning fluids.

4 Claims, 2 Drawing Sheets

FLUID-SEALED REFRACTOMETER HAVING DATA TRANSMISSION MEANS

BACKGROUND OF THE INVENTION

The present invention relates generally to refractometers for measuring refractive index of a substance, and more particularly to an automatic refractometer that includes a completely fluid-sealed housing for easy cleaning without sacrificing the capability to download measurement data to a computer.

Refractometers are widely used for quality control in industry for measuring sugar concentrations (Brix scale) of fruits, fruit juices, soft drinks and other food products; measuring concentrations of water soluble cutting fluids and other lubricants; testing the freeze point of propylene glycol and ethylene glycol antifreeze solutions; measuring the boiling point and percent water content of brake fluids; testing salinity of sea water; and for other refractive-index based measurements. Because refractometers come into contact with the above-mentioned fluids both during testing and as a natural consequence of being stored in industrial environments, they require frequent cleaning. It is therefore desirable to protect internal optics and electronics (in the case of automatic refractometers) from exposure to harmful test fluids and cleaning fluids.

While many automatic refractometers on the market today are substantially fluid-sealed, they suffer the drawback that a connection port for connecting a data cable to the instrument for downloading digital measurement data to a computer is exposed to test samples, environmental fluids, and cleaning fluids. Therefore, neatness during use and care during cleaning are required to prevent damage to the connection port. In non-automatic refractometers and refractometers without data downloading capability, completely fluid-sealed housings are known.

BRIEF SUMMARY OF THE INVENTION

Therefore, it is an object of the present invention to improve an automatic refractometer of a type that provides digital measurement data by enclosing the refractometer components in a completely fluid-sealed housing, without destroying the refractometer's capability to download measurement data to a computer.

To meet this object, a refractometer of the present invention is provided with a completely fluid-sealed housing, and a wireless transmitter is among the components enclosed within the housing. Digital measurement data are thereby transmitted as optical pulse signals through a communication window in the housing to a corresponding receiver connected to a computer. In a preferred embodiment, infrared signal transmission is in accordance with IrDA (Infrared Data Association) hardware standards.

The housing includes an upper housing portion having a sample well opening and a display panel recess, a display/button panel fitted to reside in the display panel recess, a sample well received in the sample well opening, a lower housing portion including a window recess and a battery opening, the aforementioned communication window fitted to reside in the window recess, and a battery cover threadably attached to the lower housing portion to cover the battery opening. Fluid sealing O-rings are provided at connections between the upper and lower housing portions, between the sample well and the upper housing portion, and between the battery cover and the lower housing portion.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE INVENTION

Figure 1:
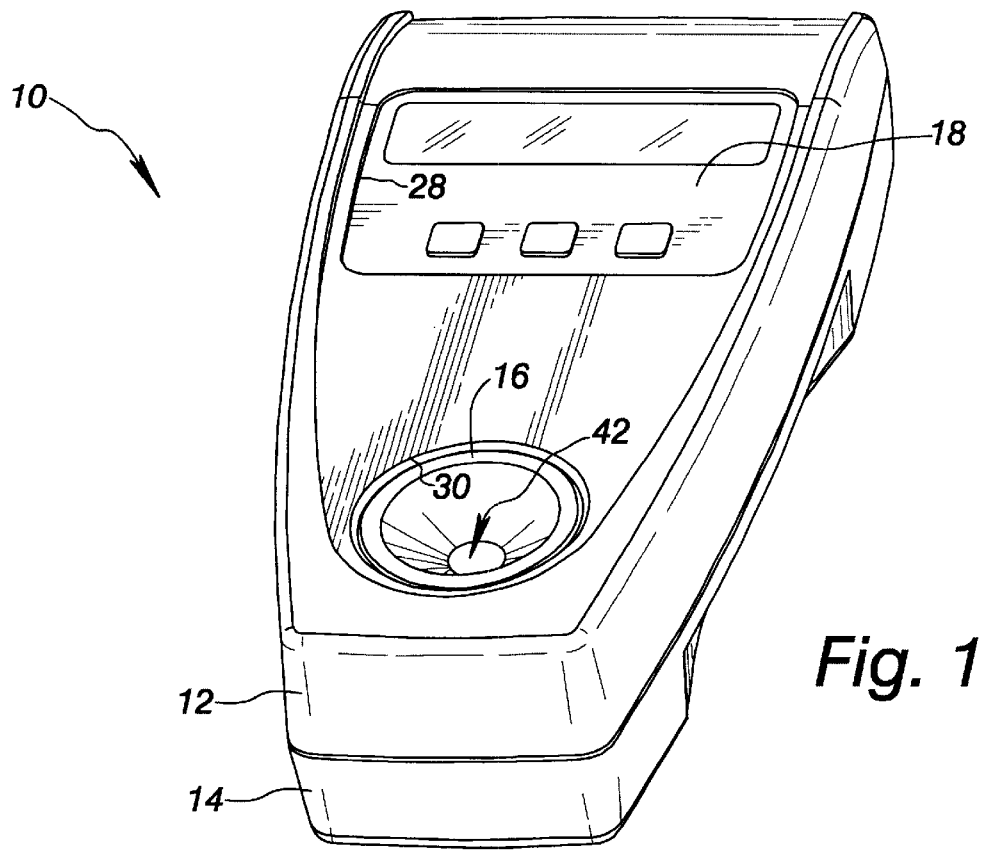
FIG. 1 is a perspective view of an automatic refractometer formed in accordance with a preferred embodiment of the present invention.
Figure 2:
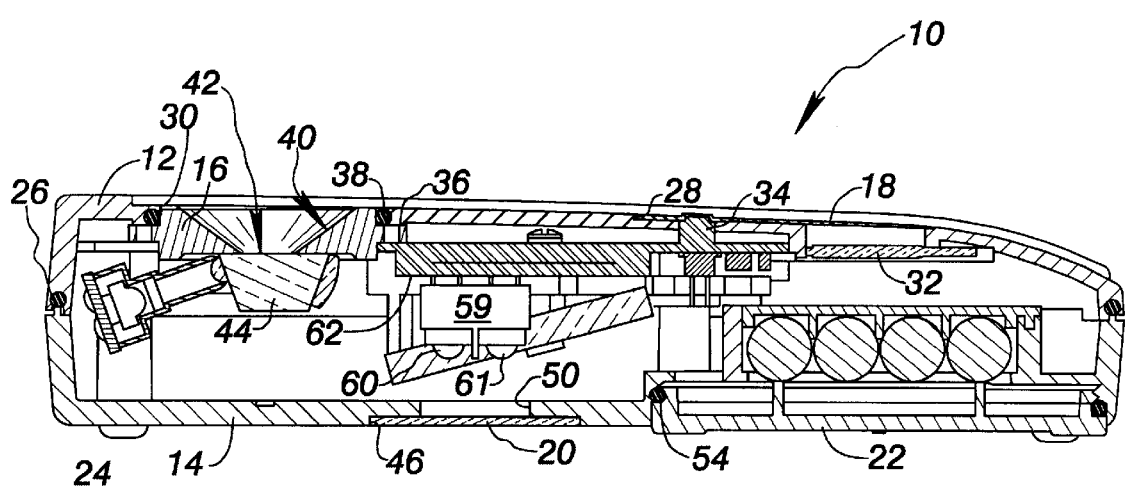
FIG. 2 is a cross-sectional view of the automatic refractometer shown in FIG. 1.
Figure 3:
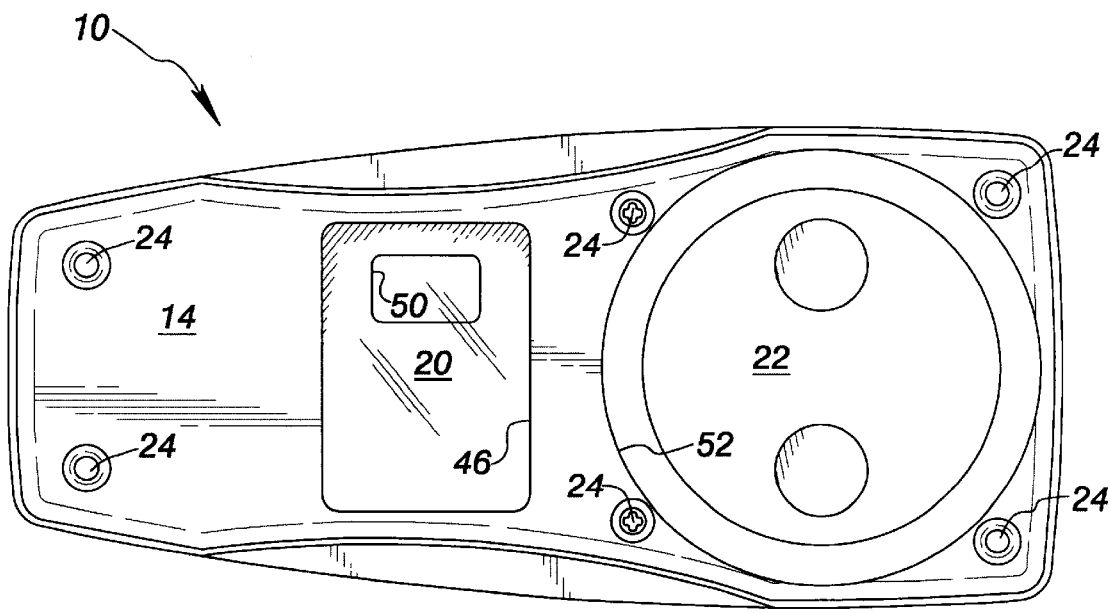
FIG. 3 is a bottom plan view of the automatic refractometer shown in FIG. 1.

Referring to FIGS. 1 through 3, an automatic hand-held refractometer formed in accordance with a preferred embodiment of the present invention is shown and broadly designated by the reference numeral 10. Refractometer 10 is of a type that provides digital measurement data. In the presently preferred embodiment, refractometer 10 uses optical means in combination with a photosensitive detector, analog-to-digital conversion electronics for digitizing output from the detector, and microprocessing electronics for evaluating the digitized information to provide digital measurement data, as taught in commonly owned U.S. patent application Ser. No. 09/842,463, which is hereby incorporated by reference in the present specification.

Refractometer 10 includes a multiple-piece assembled housing that generally comprises an upper housing portion 12, a lower housing portion 14, a sample well 16 mounted in upper housing portion 12, a display/button panel 18 mounted in upper housing portion 12, a communication window 20 mounted in lower housing portion 14, and a battery cover 22 threadably attached to lower housing portion 14.

Upper housing portion 12 and lower housing portion 14 are preferably molded plastic pieces sized for closing fit with each other about their opposing peripheries and held together by a plurality of fasteners 24. In accordance with the present invention, a sealing O-ring 26 is situated about the entire joined periphery and confined between upper housing portion 12 and lower housing portion 14 to provide a fluid-tight seal therebetween.

Upper housing portion 12 includes a display panel recess 28 sized to receive display/button panel 18 in a close-fitting manner, and a circular sample well opening 30 sized to receive an upper cylindrical portion of sample well 16. Display/button panel 18 is a fluid-tight panel cemented in display panel recess 28 to provide a fluid-sealed cover over LCD display 32 and control buttons 34. Sample well 16 includes a circumferential flange 36, and a sealing O-ring 38 is situated and confined between flange 36 and upper housing portion 12 for fluid sealing about the sample well. Sample well 16 includes a frustoconical inner wall 40 tapering to meet an external surface 42 of a sample prism 44 for receiving a test sample.

The underside of lower housing portion 14 includes a window recess 46 in which a correspondingly sized communication window 48 is cemented in a sealing manner. Communication window 48 is formed of plastic that transmits infrared radiation, and completely covers a communication portal 50 through the underside of lower housing portion 14. Lower housing portion 14 further includes a battery opening 52 through which batteries can be inserted into and removed from refractometer 10, and battery cover 22 is threadably attached to the lower housing portion to cover battery opening 52. A sealing O-ring 54 is provided between battery cover 22 and lower housing portion 14 to maintain a fluid-tight seal when the battery cover is in place.

Figure 4:
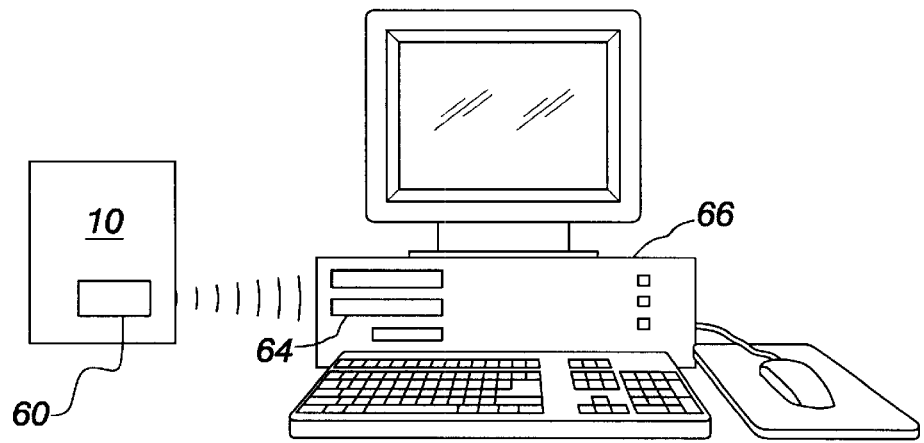
FIG. 4 is a schematic diagram showing wireless data communication of the automatic refractometer of the present invention.

Despite the completely fluid-sealed design of refractometer 10, it nevertheless is capable of transmitting its digital measurement data to an external computer. In particular, the means for downloading the data to an external computer is fully enclosed by the completely fluid-sealed housing. In accordance with the present invention, the means for downloading the data to an external computer comprises a signal transmitter for converting the digitized data into optical pulses for wireless transmission to a corresponding receiver installed in a computer. Making reference now to FIGS. 2 and 4, presently preferred data transmission means comprises a standard IrDA transceiver 59 that includes an infrared LED 60 for transmission and an infrared photodiode 61 for reception connected to a main circuit board 62 of the refractometer and arranged to closely face communication portal 50 and communication window 20. Transmitter 60 generates infrared pulse signals transmitted through communication portal 50 and communication window 20 to a corresponding IrDA transceiver 64 installed in external computer 66. Of course other wireless communication interfaces may be used, including those which operate via radio frequencies, for example a "Bluetooth" interface.

As will be appreciated from the foregoing description, refractometer 10 is completely fluid-sealed for easy cleaning. This convenience does not prevent data communication with an external computer, as was the case with refractometers of the prior art, by virtue of the enclosure of wireless data transmission means within the refractometer housing.

What is claimed is:

1. In an automatic refractometer of a type providing digital measurement data and means for downloading said data to an external computer, the improvement comprising:

a completely fluid-sealed housing enclosing said means for downloading said data.

2. The improvement according to claim 1, wherein said means for downloading said data comprises a wireless signal transmitter for communication with a receiver at said remote computer.

3. The improvement according to claim 2, wherein said wireless signal transmitter is an infra-red signal transmitter, and said housing includes a window of a material transmissive to infra-red radiation.

4. The improvement according to claim 3, wherein said window is on a bottom portion of said housing.

* * * * *